United States Patent [19]

Heidgen

[11] Patent Number: Plant 6,351

[45] Date of Patent: Oct. 25, 1988

[54] GERANIUM PLANT NAMED CONFETTI

[76] Inventor: Charles F. Heidgen, 821 Walnut St., Batavia, Ill. 60510

[21] Appl. No.: 782,731

[22] Filed: Oct. 1, 1985

[51] Int. Cl.[4] ..... A01H 5/00
[52] U.S. Cl. ..... Plt./68
[58] Field of Search ..... Plt./68

*Primary Examiner*—Robert E. Bagwill

[57] ABSTRACT

A new and distinct variety of geranium plant, Confetti, characterized by its cascading growth habit; its continuous and exceptionally prolific blooming habit; its small, medium to dark green foliage; its distinctive pink and almost white centered single flower; and its heat tolerance.

1 Drawing Sheet

The present discovery, hereinafter referred to by the cultivar name, Confetti, relates to a new and distinct geranium plant.

BACKGROUND

Confetti is a new and improved variety which has resulted from definite breeding programs and experiments carried on by me in my greenhouses at 821 Walnut St., Batavia, Ill. Our experiments commenced in March, 1977 and are being carried on continuously. This seedling, is a selection seedling from unmonitored crosses from unpatented dwarf and semi-dwarf geranium varieties.

Asexual reproduction of Confetti has been accomplished from vegetative cutting in my greenhouses in Batavia, Ill. Examination of plants so propagated has demonstrated that the combination of characteristics herein disclosed for Confetti are firmly fixed and retained through successive generations of asexual reproduction.

SUMMARY

The new and patentable characteristics of Confetti reside in its cascading growth habit, its continuous and exceptionally prolific blooming habit, its small, medium to dark green foliage, its distinctive pink and white centered flowers that are single, and its heat tolerance.

DESCRIPTION OF DRAWING

The photograph shows the plant and flower of a fully developed geranium of the new variety, Confetti.

BOTANIC DESCRIPTION

The Plant

Growth: Confetti is an exceptionally prolific bloomer. The florets are single, with the two upper petals somewhat narrower and shorter than the three lower petals. The flower head (truss) is of medium size and not very resistant to shattering. The growth is procumbent in habit giving a cascading effect. Growth rate is rapid, producing a typical 10" flowering basket in 10–12 weeks from four 2¼" plants using standard commercial culture.

Blooming habit: Exceptionally prolific and continuous bloomer, throughout the year, outdoors or in the greenhouse. A mature 10" basket commonly produces 20–26 heads at one time.

Inflorescence: Medium-size, open head, somewhat rounded, measuring 3½–4 inches in diameter.

Foliage:
- *Quantity.*—Abundant.
- *Size.*—Small, 1¼–2½ inches across.
- *Color.*—Spinach Green (0960/3) with Spinach Green (0960) zone. (The Royal Horticultural Society Horticultural Colour Chart).

Stem: Slim, short internodes, free branching, procumbent habit, rapid grower.

Petiole: Short, slightly longer than leaf. Same color as leaf.

The Flower

Truss:
- *Size.*—Medium-size, 3½–4 inches in diameter.
- *Shape.*—Open, a flattened globe as it opens.
- *Number of florets.*—Variable, range from 5–16, average 10–11.
- *Lasting quality.*—Average. Blooms remain 5–12 days, longer if cool and dry.

Bud:
- *Sepals.*—Short, slightly pointed.
- *Color.*—Rose Opal (022) (The Royal Horticultural Society Horticultural Colour Chart).
- *Form.*—Pointed.

Florets:
- *Size.*—1¼–1½ inches.
- *Petalage.*—Single, five.
- *Color.*—Rose Madder (23) at the edge and Rose Pink (427/3) toward the center. (The Royal Horticultural Society Horticultural Colour Chart).

Texture: Soft and light.

Form: Somewhat primitive, upper petals ¼" wide, lower petals ⅜" wide.

Lasting quality: Average floret lasts 4–8 days. The truss lasts up to 8–11 days.

Behavior: Once the plant begins to bloom, its exceptionally prolific blooming habit yields a striking display of white centered, pink blossoms against the smallish medium to dark green leaves.

Having thus disclosed my invention, I claim:

1. A new and distinct variety of geranium plant, substantially as shown and described, characterized by its cascading growth habit; its continuous and exceptionally prolific blooming habit; its small, medium to dark green foliage; its distinctive pink and almost white centered single flower; and its heat tolerance.

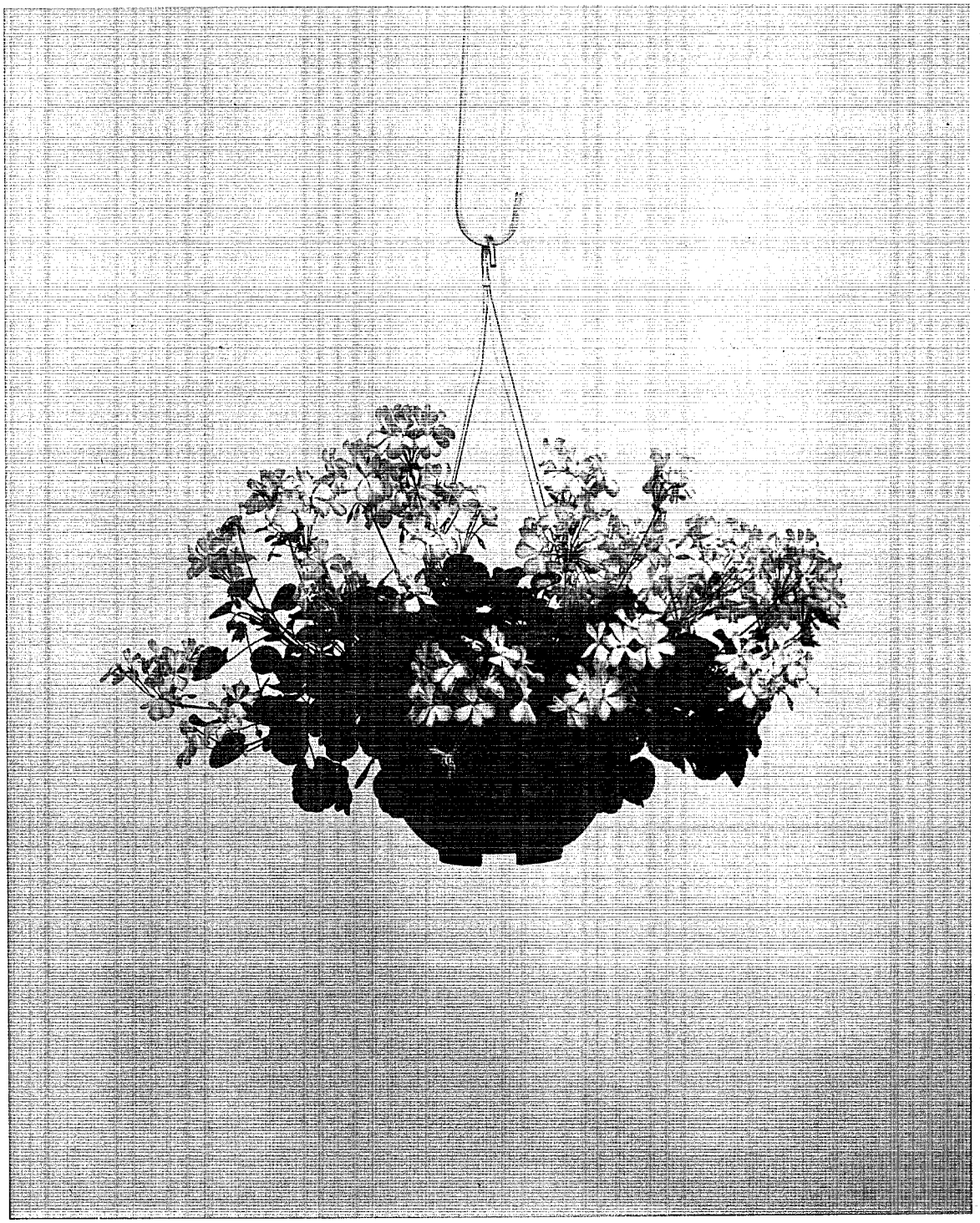

* * * * *